United States Patent [19]
Gehrich et al.

[11] Patent Number: 4,989,606
[45] Date of Patent: Feb. 5, 1991

[54] INTRAVASCULAR BLOOD GAS SENSING SYSTEM

[75] Inventors: John L. Gehrich, Laguna Beach; Thomas P. Maxwell, Santa Ana; Thomas G. Hacker, Anaheim, all of Calif.

[73] Assignee: Minnesota Mining and Manufactoring Company, St. Paul, Minn.

[21] Appl. No.: 229,617

[22] Filed: Aug. 8, 1988

Related U.S. Application Data

[63] Continuation-in-part of Ser. No. 8,937, Jan. 30, 1987, Pat. No. 4,830,013.

[51] Int. Cl.$^5$ .................................................. A61B 5/00
[52] U.S. Cl. ..................................... 128/637; 128/665; 128/666; 128/DIG. 13
[58] Field of Search ............... 128/637, 634, 665, 666, 128/DIG. 12, DIG. 13; 364/413.06, 413.07, 413.08, 413.09; 604/4-6

[56] References Cited

U.S. PATENT DOCUMENTS

| | | | |
|---|---|---|---|
| Re. 31,879 | 5/1985 | Lubbers et al. | 436/133 |
| 2,629,399 | 2/1953 | Kulick | 128/632 |
| 3,433,935 | 3/1969 | Sherman | 128/667 |
| 3,461,856 | 8/1969 | Polanyi | 128/637 |
| 3,498,286 | 3/1970 | Polanyi et al. | 128/637 |
| 3,512,517 | 5/1970 | Kadish et al. | 128/637 |
| 3,529,591 | 9/1970 | Schuette | 128/637 |
| 3,612,866 | 10/1971 | Stevens | 250/106 |
| 3,616,409 | 10/1971 | Tosteson | 204/195 |
| 3,658,053 | 4/1972 | Fergusson et al. | 73/23 |
| 3,674,013 | 7/1972 | Polanyl | 356/241 |
| 3,807,390 | 4/1974 | Ostrowski et al. | 356/41 |
| 3,814,081 | 6/1974 | Mori | 128/667 |
| 3,841,308 | 10/1974 | Tate | 128/667 |
| 3,866,599 | 2/1975 | Johnson | 128/634 |
| 3,878,830 | 4/1975 | Bicher | 128/667 |
| 3,893,448 | 7/1975 | Brantigan | 128/348 |
| 3,983,864 | 10/1976 | Sielaff et al. | 128/637 |
| 4,008,717 | 2/1977 | Kowarski | 128/632 |
| 4,016,864 | 4/1977 | Sielaff et al. | 128/637 |
| 4,050,450 | 9/1977 | Polanyi | 356/41 |
| 4,073,279 | 2/1978 | Kopp | 128/DIG. 16 |
| 4,120,292 | 10/1978 | LeBlanc, Jr. et al. | 128/637 |
| 4,187,856 | 2/1980 | Hall et al. | 128/635 |
| 4,200,110 | 4/1980 | Peterson et al. | 128/634 |

(List continued on next page.)

FOREIGN PATENT DOCUMENTS

| | | | |
|---|---|---|---|
| 0276977 | 1/1988 | European Pat. Off. | |
| 8401109 | 9/1983 | PCT Int'l Appl. | |
| 1593270 | 7/1981 | United Kingdom | 127/667 |

OTHER PUBLICATIONS

IEEE Transactions on Biomedical Engineering, vol. BME-33, No. 2, Feb. 1986, pp. 117-132, IEEE, New York; J. L. Gehrich et al; "Optical Fluorescence and its Application to an Intravascular Blood Gas Monitoring System".

Primary Examiner—Francis Jaworski
Assistant Examiner—George Manuel
Attorney, Agent, or Firm—Donald M. Sell; Walter N. Kirn; Dale E. Hulse

[57] ABSTRACT

An assembly useful in conjunction with a signal transmission means for the measurement of a compositional parameter of the blood of a patient is disclosed. This assembly comprises a housing adapted and sized to be located outside the body of a patient and having a fluid flow passage therethrough into which blood from the patient is passed from a hollow tube, the fluid flow passage being defined by a wall which is substantially impermeable to blood, the housing being adapted to be removeably secured to a signal transmission system such that the housing is capable of being removed from the signal transmission system without disrupting the fluid flow passage; and a sensing element located in the housing in or near the fluid flow passage for providing a signal directly to the signal transmission system in response to a compositional parameter of blood located in the fluid flow passage.

36 Claims, 4 Drawing Sheets

U.S. PATENT DOCUMENTS

| | | | |
|---|---|---|---|
| 4,201,222 | 5/1980 | Haase | 128/634 |
| 4,210,029 | 7/1980 | Porter | 128/634 |
| 4,265,249 | 5/1981 | Schindler et al. | 128/635 |
| 4,274,417 | 6/1981 | Delpy | 128/632 |
| 4,295,470 | 10/1981 | Shaw et al. | 128/634 |
| 4,311,137 | 1/1982 | Gerard | 128/DIG. 16 |
| 4,322,164 | 3/1982 | Shaw et al. | 356/243 |
| 4,360,615 | 7/1982 | Goodwin et al. | 427/2 |
| 4,398,542 | 8/1983 | Cunningham et al. | 128/675 |
| 4,407,290 | 10/1983 | Wilber | 364/413.09 |
| 4,471,765 | 9/1984 | Strauss | 128/655 |
| 4,476,870 | 10/1984 | Peterson et al. | 128/634 |
| 4,476,877 | 10/1984 | Barker | 128/736 |
| 4,478,222 | 10/1984 | Koning et al. | 128/632 |
| 4,502,488 | 3/1985 | Degironimo et al. | 128/692 |
| 4,508,123 | 4/1985 | Wyatt et al. | 128/692 |
| 4,535,786 | 8/1985 | Kater | 128/760 |
| 4,543,961 | 10/1985 | Brown | 128/667 |
| 4,557,900 | 12/1985 | Heitzmann | 422/55 |
| 4,573,968 | 3/1986 | Parker | 604/67 |
| 4,585,007 | 3/1986 | Uchigaki et al. | 128/632 |
| 4,601,706 | 7/1986 | Aillon | 604/122 |
| 4,608,996 | 9/1986 | Brown | 128/760 |
| 4,640,820 | 2/1987 | Cooper | 422/68 |
| 4,651,741 | 3/1987 | Passafaro | 128/633 |
| 4,684,245 | 8/1987 | Goldring | 364/413.09 |
| 4,718,423 | 1/1988 | Willis et al. | 128/634 |
| 4,736,748 | 3/1988 | Nakamura et al. | 128/632 |
| 4,774,955 | 10/1988 | Jones | 128/632 |
| 4,785,814 | 11/1988 | Kane | 128/634 |
| 4,810,655 | 3/1989 | Khalil et al. | 436/138 |
| 4,830,013 | 5/1989 | Maxwell | 128/637 |

INTRAVASCULAR BLOOD GAS SENSING SYSTEM

RELATED APPLICATION

This application is a continuation-in-part of copending application Ser. No. 008,937, filed Jan. 30, 1987 now U.S. Pat. No. 4,830,013.

BACKGROUND OF THE INVENTION

It is often necessary or desirable to measure various parameters of blood, such as temperature, pressure and compositional parameters of blood, i.e., the presence and/or concentration of blood constituents, such as blood gases, hydrogen ions (pH), other electrolytes, glucose, red blood cells and the like. Measurement of compositional parameters of blood can be accomplished in real time using fluorescent sensors. For example, this can be accomplished in an extracorporeal blood loop as shown in Cooper U.S. Pat. No. 4,640,820 and in vivo as disclosed in Lubbers et al Reissue Patent No. 31,879. The system disclosed in this Cooper patent involves a fluid (blood) passageway partly defined by membranes which are permeable to one or more blood constituents. For in vivo sensing, a probe or catheter carrying an appropriate sensor is inserted into a blood vessel of the patient. Because blood vessels are quite small, sensors designed to be inserted in such vessels must be very small. This size constraint may have a detrimental effect on the accuracy of the determination made by the sensor.

Kater U.S. Pat. No. 4,535,786 discloses a method and apparatus for measuring parameters of body fluids, e.g., blood, using sensing electrodes which are calibrated periodically. Kater discloses a system in which the sensing electrodes are located at a relatively large area of the blood path. That is, the cross-sectional area of the blood path is increased relative to the cross-sectional area of this path immediately upstream of the sensing electrodes. Thus, a relatively large volume of blood must be drawn from the patient in order to obtain the desired measurements with the system.

Parker U.S. Pat. No. 4,573,968 discloses a system in which blood drawn from a patient into a cassette comes into direct contact with electrochemical sensors which are mounted along a flow path inside the cassette. The wires leading from the cassette to the analyzer appear to be an integral part of the cassette. Thus, both the cassette and the wires of the Parker system require disposal after use, in order to avoid blood contamination between patients. The Kater system has similar disposal concerns. It would be advantageous to have to dispose of as little as possible in order to minimize costs.

Other patents which have been considered in preparing the application include Kulick U.S. Pat. No. 2,629,399; Cunningham et al U.S. Pat. No. 4,398,542; Koning et al U.S. Pat. No. 4,478,222; and Heitzmann U.S. Pat. No. 4,557,900.

SUMMARY OF THE INVENTION

The present invention is based in part on the recognition and discovery that only a small amount of blood is needed to obtain accurate and reliable blood analyses. Thus, for example, a system which is structured to draw a relatively limited amount of blood from a patient can provide satisfactory measurements. Further, by isolating the blood flow path from the more expensive analytical equipment, the component which includes the flow path can be economically and effectively disposed of after use, thereby avoiding cross-patient blood contamination. The sensing element of the present system is advantageously located outside the body of the patient, and a housing which carries the sensor is preferably sufficiently compact so that it can be attached to the body, e.g., arm, of the patient.

In one broad aspect, the present invention involves an assembly useful for the measurement of a compositional parameter of the blood of a patient. This assembly comprises a housing containing a fluid flow passage, and a sensing element located in or near such passage. The housing is preferably adapted and sized to be located outside the patient's body. The fluid flow passage extends through the housing. Blood, from a hollow tube in fluid communication with a blood vessel of the patient, is passed in and out of this flow passage. The fluid flow passage is defined by a wall which is substantially impermeable to the blood in the passage. Thus, the passage and housing can be effectively isolated from other components, such as signal transmitting wires, optical fibers and the like, so that after use by one patient the housing can be easily disposed of without requiring that such other components be disposed of as well. This feature results in substantial cost economies and protects individual patients from being exposed to cross-patient blood contamination. The sensing element acts to provide a signal to a signal transmission means or system in response to a compositional parameter of blood located in the fluid flow passage.

In one embodiment, the assembly is structured so that the housing can be removed from the signal transmission means, preferably without disrupting the fluid flow passage. In this embodiment, the flow passage is entirely isolated from the signal transmission system so that, for example, the signal transmission means can be easily separated from the housing, e.g., to allow easy disposal of the housing, as desired. As used in the context of this paragraph, the term "signal transmission means or system" includes those components which are provided with a signal directly from the sensing element. For example, if the sensor is electrochemical in nature, the signal transmission means includes the wires directly secured to the sensors; and if the sensing element is an optical sensing element, the signal transmission means or system includes the optical fiber or fibers which receive signals directly from the sensing element.

A further embodiment involves a geometrical variation of the fluid flow passage. In this embodiment the fluid flow passage is at least two times as wide as it is deep at or near the location of the sensing element. The "deep" direction extends directly outwardly from the sensing element. The "wide" direction is the direction substantially perpendicular to both the general direction of fluid flow in the passage and to the deep direction. This feature advantageously increases the effective amount or fraction of blood exposed to the sensing element. Thus, this fluid flow passage geometry makes very effective use of the blood, e.g., a relatively limited amount of blood, in the passage.

The size and configuration of the fluid flow passage preferably are such that blood can be conveniently drawn through the hollow tube into the fluid flow passage from the patient for analysis and, after analysis, the blood can be substantially completely removed from the passage through the hollow tube back to the patient. In other words, the size and configuration of the fluid flow passage are preferably such that the blood is substantially completely removed from the passage back to the patient, e.g., through the action of a conventional flush fluid which also passes to the patient. Substantially no blood remains in the passage to coagulate or otherwise adversely affect the patient or the present system. The crosssectional area of the fluid flow passage at or near the location of the sensing element is preferably less than about 10 times, more preferably less than about 3 times, as large as the largest cross-sectional area of the hollow tube available for fluid flow between the patient and the passage. The cross-sectional area of the fluid flow passage at or near the location of the sensing element may be about the same as the largest cross-sectional area of the hollow tube. This feature reduces the amount of blood needed to be drawn from the patient. It has been found that reliably accurate measurements can be obtained with this relatively limited amount of blood in the fluid flow passage. Reducing the amount of blood drawn also reduces any harmful impact on the patient caused by having the blood flow in the fluid flow passage.

In certain embodiments, the housing preferably includes a first housing component and a second housing components. Thus, for example, the first housing component may include a first recess and the second housing component may include a second recess. The first and second housing components are located so that each of the first and second recesses forms a part of the fluid flow passage. A substantially annular space, which is formed between the two housing components, is at least partially filled with an adhesive to bond the two housing components together. This housing structure is very useful and relatively easy to manufacture.

Another useful configuration involves a first housing component which defines a portion of the fluid flow passage and includes first and second tubing fittings acting to secure first and second segments of hollow tubing, respectively, to the housing. The first housing component also includes first portions of first and second channels each of which terminate in the fluid flow passage. The second housing component also defines a portion of the fluid flow passage and includes second portions of the first and second channels. This construction is very convenient and advantageous in using the first and second channels to provide relatively smooth transitioning of the flow of blood between the hollow tubing segments and the fluid flow passage. In addition, fabricating and assembling housing components structured as described above is cost effective, particularly when the materials of construction are polymeric materials.

The housing preferably includes first and second tubing fittings which are located adjacent opposing ends of the fluid flow passage and are adapted to hold first and second segments of hollow tubing, respectively to the housing. These tubing fittings are preferably structured so that the first and second segments of hollow tubing are orientated in mutually substantially opposing directions, substantially perpendicular to the general direction of flow in the fluid flow passage. The mutually substantially opposing directions are preferably substantially co-planar and/or are substantially parallel to the surface of the part of the patient's body to which the assembly is attached. Such orientation reduces the risk of the tubing segments becoming entangled, crimped or otherwise obstructed during use of the assembly. Thus, blood can flow freely in and out of the tubing segments without stagnating.

The housing preferably includes a recess which is sized and adapted to receive a portion, e.g., the distal end, of the signal transmission means when the housing is removably secured to the signal transmission means. This recessed structure of the housing allows the housing to be very easily and conveniently "mated" to the signal transmission means for use. The signal transmission means preferably includes a releasable coupling means which can be activated to removably secure the housing to the signal transmission means. Such coupling means allows the housing to be conveniently coupled or decoupled from the signal transmission means, as desired.

In yet another embodiment, the fluid flow passage has a first wall and a substantially opposing second wall and the signal transmission means includes a releasable coupling means. The housing is preferably structured so that the coupling means contacts the housing at a location adjacent the second wall to hold the housing in removable securement (removably coupled) to the signal transmission means. In a particularly useful embodiment, the housing includes a first housing portion with the first wall of the fluid flow passage; and a second housing portion fixedly secured to the first portion and including the second wall of the fluid flow passage. The second housing portion is adapted to be contacted by the coupling means to hold the housing in removable securement to the signal transmission means. Preferably, the first housing portion includes the sensing element. This feature provides an effective way to removably secure the housing to the signal transmission means. It is preferred that the housing and signal transmission means be structured to be capable of being removably secured in a manner so that effective signal communication between the sensing element and the signal transmission means is provided.

Each of the features discussed herein may be used alone or in any combination, as may be desired to satisfy a given application.

The sensing element or elements useful in the present system are preferably optical sensing elements, for example sensing elements based on light fluorescence or absorbance. More preferably, the sensing element is a fluorescent sensing element. Where optical sensing elements are employed, the assembly further comprises signal transmission means, in particular including optical fibers, for transmitting signals from the sensing elements. In one useful embodiment where an optical sensing element is employed, the housing includes a substantially transparent or optically clear (i.e., at the signal wavelength or wavelengths of interest) first housing component through which an optical signal is provided to the signal transmission means in response to a compositional parameter of blood located in the fluid flow passage, and a substantially gas impermeable second housing component which forms part of the fluid flow passage. This is particularly useful where one or more blood gases are to be sensed and provides for increased sensing accuracy since a reduced amount of blood gas permeates through and escapes from the housing. In this embodiment, it is particularly preferred that the first and second housing components be made of different materials.

The sensing element is located so that substantially accurate determinations of the compositional parameter of interest of the blood in the fluid flow passage are obtained. The sensing element or elements may be located so as to be in direct contact with the housing or such element or elements may be situated so as to be physically separated from the housing. This "physical separation" embodiment is particularly useful where the sensing element is used to determine the concentration of a blood gas, such as oxygen and carbon dioxide, and provides for more accurate determinations. Such physical separation is achieved, for example, by locating the sensing element on a support element which itself physically contacts, e.g., is secured to, the housing. This support element, which may be made out of glass and the like materials, is preferably substantially impermeable to blood gases, and preferably is substantially transparent.

In one useful embodiment, the present system preferably comprises a plurality of sensing elements, with each of the sensing elements providing a signal to a signal transmission means in response to a different compositional parameter of blood located in the fluid flow passage.

The present assembly may further comprise a volume oscillator means in fluid communication with the fluid flow passage. This volume oscillator means urges blood from the patient to flow in the fluid flow passage. The volume oscillator means is preferably structured and located so that substantially no net pumping of blood results from the operation of the volume oscillator means.

The invention, together with additional features and advantages thereof, may best be understood by reference to the following description taken in connection with the accompanying illustrative drawings.

DETAILED DESCRIPTION OF THE DRAWINGS

Figure 1:
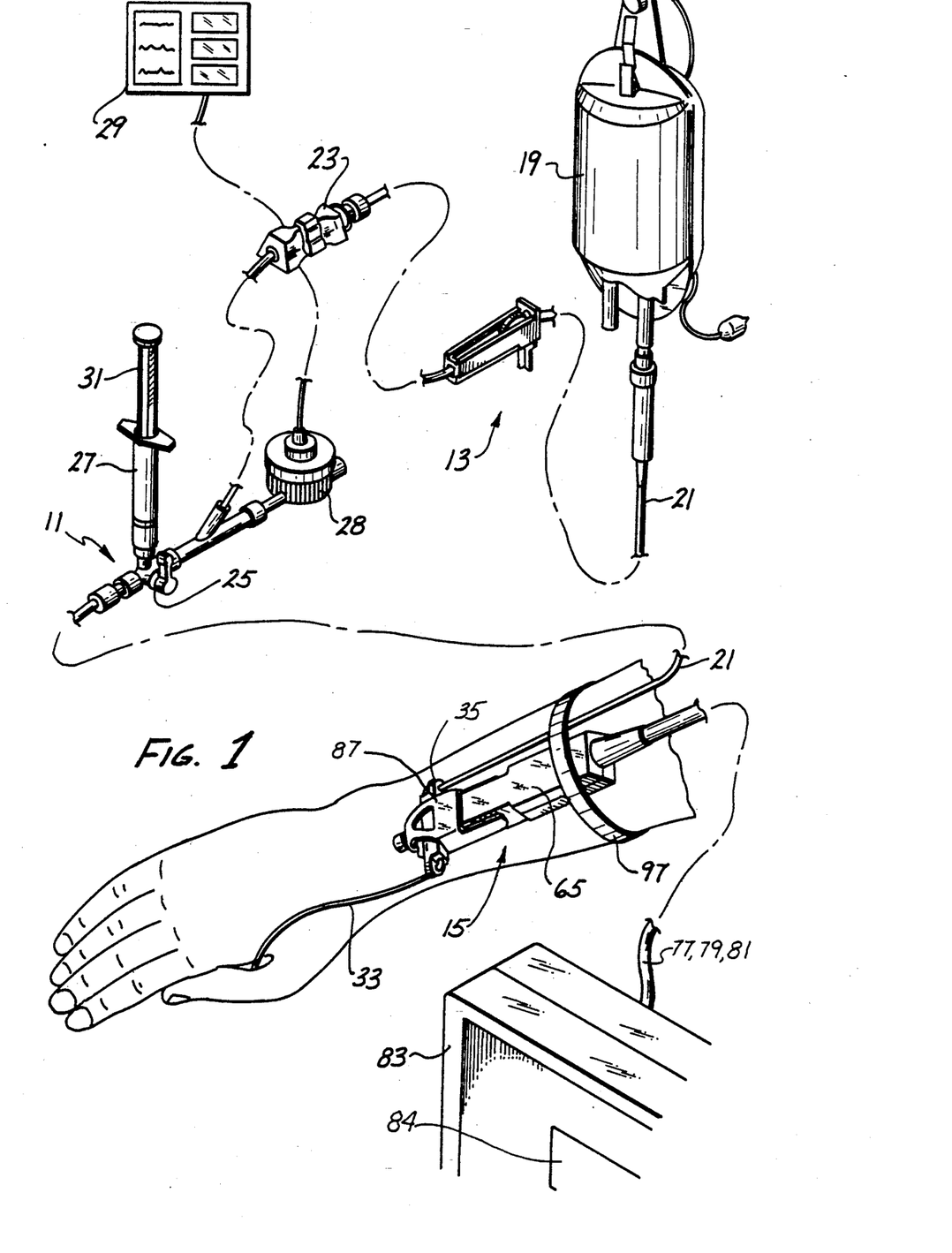
FIG. 1 is a schematic illustration showing one embodiment of the present assembly in use.
Figure 2:
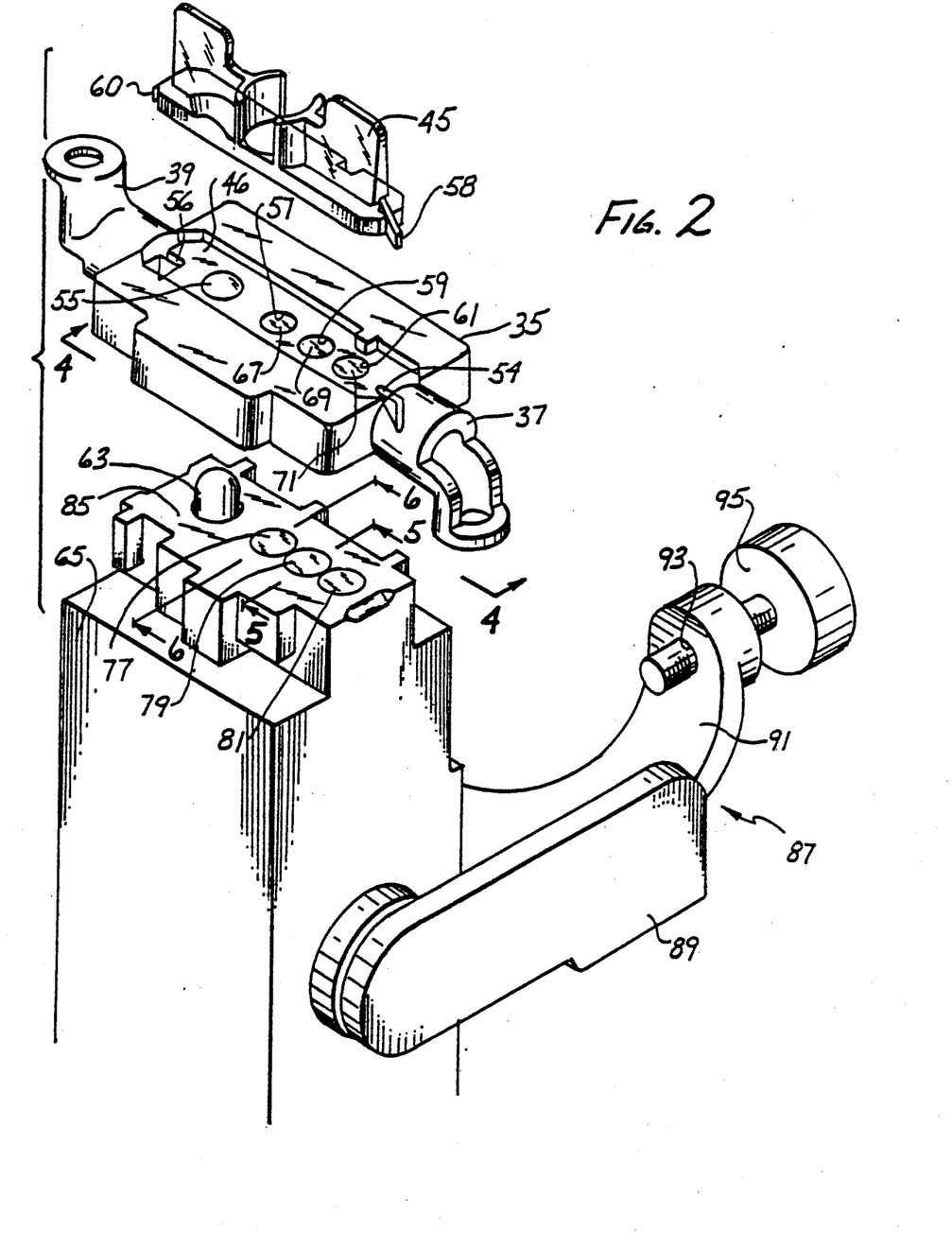
FIG. 2 is an exploded view, in perspective, of certain components of the embodiment of the present assembly shown in FIG. 1.

FIG. 1 shows an assembly 11 for the measurement of various blood compositional parameters, and particularly the pH value and the concentrations of oxygen and carbon dioxide of blood. Although the assembly 11 can be of different constructions, in this embodiment it includes a solution introducing system 13 and a sensor assembly 15.

Generally, the solution introducing system 13 introduces an appropriate flush solution, e.g., an anticlotting solution, such as a heparinized saline solution, through various components of the sensor assembly 15 to the patient to keep the line leading to the patient patent.

Although this can be accomplished in different ways, in the embodiment shown schematically in FIG. 1, the system 13 includes a pressurized source 19 of heparinized saline solution, a first conduit 21 leading from the source to the sensor assembly 15, a drip control and rapid flush valve 23, a stopcock 25, a volume oscillator 27, a pressure transducer 28, and a pressure monitor 29. Many of the components of the solution introducing system 13 may be conventional, and this system may include other components, if desired.

In the illustrated embodiment, solution from the pressurized source 19 flows through the valve 23 at a relatively slow rate, such as 2 to 5 ml/hour. The solution flows through the first conduit 21, past the volume oscillator 27, through various components of the sensor assembly 15 to the patient. If a more rapid flow rate from the source 19 is desired, as for example during priming, the valve 23 can be manually opened to provide a relatively high solution flow rate.

Volume oscillator 27 may have any one of a number of different structures and configurations. The embodiment illustrated is a cylinder/piston type syringe which is capable of drawing a vacuum in first conduit 21 by manually moving piston 31 away from stopcock 25. This vacuum can be released by manually moving piston 31 toward stopcock 25. There is no net or average flow or pumping of blood in either direction as a result of reciprocation of the plunger 31.

Stopcock 25 can be manipulated into position (1) in which volume oscillator 27 is effectively out of the system or position (2) in which the volume oscillator 27 is in direct fluid communication with that part of first conduit 21 downstream (based on the general direction of flow of the flush fluid from source 19) from stopcock 25, and that part of first conduit 21 upstream from stopcock 25 is isolated from the remainder of the solution introducing system 13.

The pressure transducer 28 communicates with the first conduit 21 and can measure the pressure therein. Accordingly, with the second conduit 33 in fluid communication with the vascular system of a patient, the pressure transducer 28 can provide blood pressure readings. By placing stopcock 25 in position (1), the volume oscillator 27 does not affect the blood pressure readings provided by the transducer 28.

Figures 3, 5, 8:
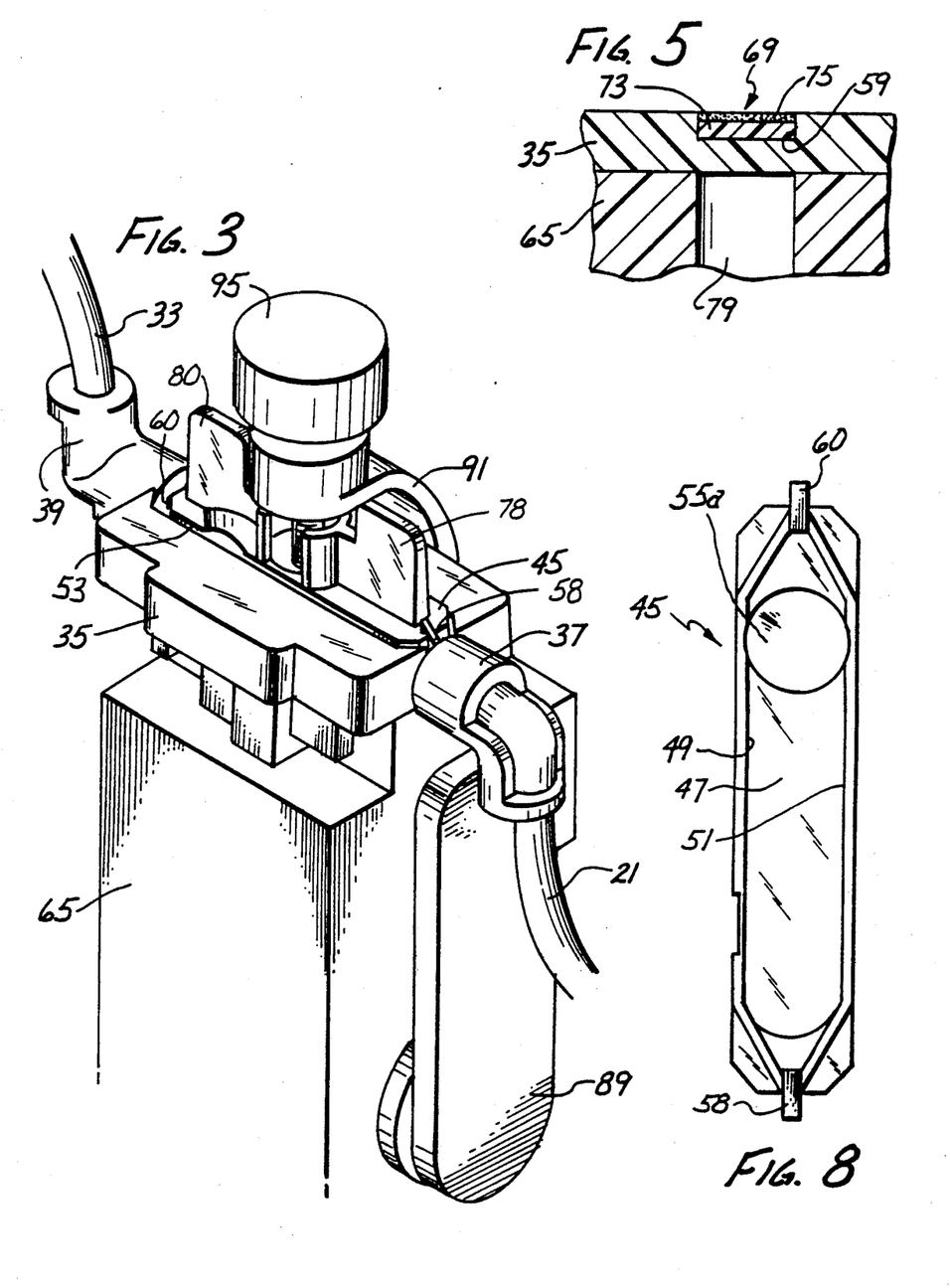
FIG. 3 is a perspective view of the components in FIG. 2 shown assembled and ready for use.
FIG. 5 is a cross-sectional view taken along line 5—5 of FIG. 2.
FIG. 8 is a bottom plan view of one of the housing components (the housing top) of the embodiment of the present assembly shown in FIG. 1.
Figures 4, 6, 7:
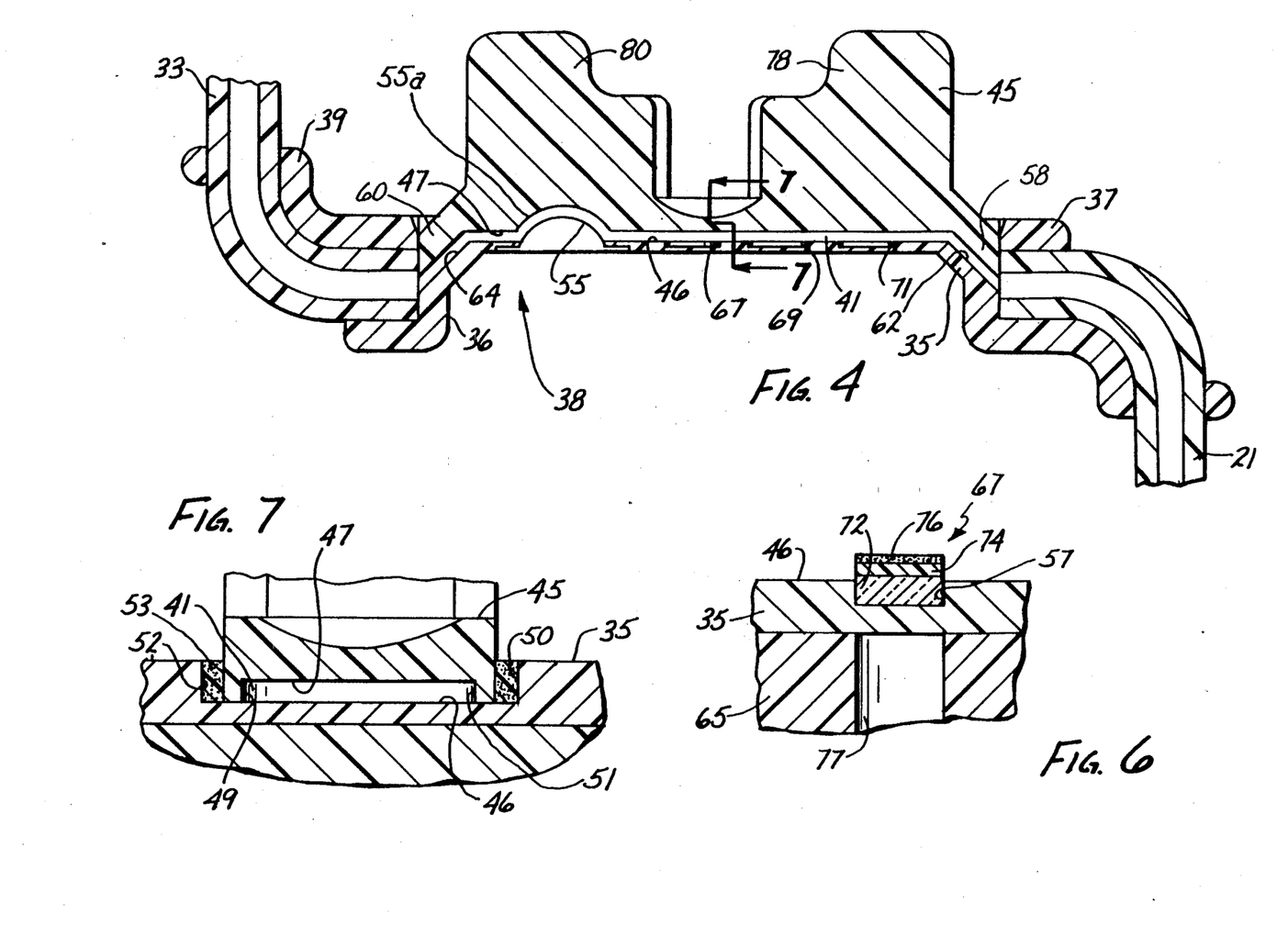
FIG. 4 is a cross-sectional view taken along line 4—4 of FIG. 2.
FIG. 6 is a cross-sectional view taken along line 6—6 of FIG. 2.
FIG. 7 is a cross-sectional view taken along line 7—7 of FIG. 4.

FIGS. 2 to 8 show various components of the sensor assembly 15. A housing base 35 is located between first conduit 21 and second conduit 33. Housing base 35 includes a first tubing fitting 37, which is secured directly to first conduit 21, and a second tubing fitting 39, which is secured directly to second conduit 33. A fluid passage 41 is located between housing base 35 and housing top 45. The housing base 35 and the housing top 45 cooperate to form a sensor cassette. As shown in FIGS. 1–4, the first and second tubing fittings 37 and 39 are configured so that tubing retention sections thereof and the first and second conduits 21 and 33 are oriented (out of housing base 35) in mutually opposing, coplanar directions perpendicular to the general directions of flow through fluid passage 41. As can be seen in FIG. 1, these mutually opposing directions are generally parallel to the surface of the patient's arm on which sensor assembly 15 is located. Housing base 35 includes a first recess which is defined by bottom wall 46 and first recess sidewall 50 and second recess sidewall 52. Housing top 45 includes a second recess which is defined by top wall 47, first sidewall 49 and second side wall 51. A fluid passage 41 is formed by placing housing top 45 in contact with bottom wall 46 of housing base 45, as best shown in FIG. 7. An adhesive 53 is placed in the substantially annular space formed between housing top 45 and housing base 35. The bottom wall 46, top wall 47, first sidewall 49 and second sidewall 51 define fluid passage 41.

An edge 36 extends around the underside periphery of housing base 35 and forms a recess 38.

Housing base 35 includes a first hole 54 and a second hole 56 which are in fluid communication with first tubing fitting 37 and second tubing fitting 39, respectively. Housing top 45 includes a first tab 58 and a second tab 60 which fit into first and second holes 54 and 56, respectively, to form first and second channels 62 and 64. These channels 62 and 64 provide flow paths for blood from first and second conduits 21 and 33, respectively, and from end portions of the fluid passage 41.

Fluid passage 41 has a cross-sectional area which is about 2.2 times the largest cross-sectional area available for fluid flow of either first conduit 21 or second conduit 33. Also, the distance between the first sidewall 49 and the second sidewall 51 of fluid passage 41 as shown in FIG. 7 is about 4.8 times the shortest distance between the top wall 47 and the bottom wall 46 of fluid passage 41.

The bottom wall 46 of fluid passage 41 includes a raised area 55 and three (3) circular indents 57, 59 and 61. Top wall 47 of housing top 45 includes a corresponding raised area 55a. The raised areas 55 and 55a are adapted to receive the distal end of the thermistor 63 which is located on the transmission block 65. During normal use, housing base 35 is held in close proximity to transmission block 65 so that the distal end of thermistor 63 extends into raised area 55. In this position, thermistor 63 is able to provide an accurate reading of the temperature of the blood in fluid passage 41.

Each of the indents 57, 59 and 61 is associated with a different one of sensors 67, 69 and 71, respectively. In this embodiment, each of the sensors 67, 69 and 71 includes a different fluorescent optical indicator. The indicators in sensors 67, 69 and 71 respond to the concentration of carbon dioxide, the pH and the concentration of oxygen, respectively, in the patient's blood to provide optical signals indicative of the compositional parameter sensed.

In general, sensors 67, 69 and 71 can be structured so that the optical indicator is incorporated or combined with a matrix material, e.g., a polymer matrix material. In particular, sensor 69 is structured as shown in FIG. 5. Sensor 69 includes an optical indicator sensitive to the pH of blood embedded in a hydrophilic polymer 73 which is placed in indent 59. Hydrophilic polymer 73 is permeable to the component, hydrogen ions, in the blood to be sensed. An opaque overcoat 75, is placed on top of polymer 73 and serves to optically isolate sensor 69 from the external environment. Overcoat 75 is permeable to the component to be sensed.

FIG. 6 illustrates the structure of sensor 67. It should be understood that sensor 71 is structured similarly to sensor 67. Sensor 67 involves a glass disc or support element 72 which is substantially transparent or optically clear to the signals sent to and transmitted by sensor 67 and is sized to fit into indent 57 and to extend a slight distance above the bottom wall 46 of fluid passage 41. Sensor 67 is constructed by placing a polymer 74, including an optical indicator sensitive to the concentration of carbon dioxide in blood, on glass disc 72. Polymer 74 is permeable to the component, carbon dioxide, in the blood to be sensed. As seen in FIG. 6, the glass disc 72 physically separates the polymer 74 from the housing base 35. An opaque overcoat 76, is placed on top of polymer 74 and serves to optically isolate the sensor 67 from the external environment. Overcoat 76 is permeable to the component to be sensed. The glass disc 72 is then placed in recess 57 and secured, e.g., adhesively secured, in place. This structure is preferred for carbon dioxide sensor 67 and oxygen sensor 71 since hydrophilic polymer 74 and overcoat 76 are physically separated from housing base 35 so that interference from housing base 35 is reduced and more accurate concentration determinations are often obtained. In addition, such structure is relatively easy to manufacture.

In addition to thermistor 63, transmission block 65 carries optical fibers 77, 79 and 81, which are designed and structured to excite, and transmit signals from, sensors 67, 69 and 71, respectively. Fibers 77, 79 and 81 transmit signals from sensors 67, 69 and 71, respectively, to an instrument 83 which includes a display module 84. Instrument 83 processes the signals from sensors 67, 69 and 71 and provides a display of the current carbon dioxide concentration, pH and oxygen concentration of the patient's blood.

Housing top 45 includes two outwardly extending wings 78 and 80 which are useful to effectively hold housing top 45 during manufacture of the housing from housing base 35 and housing top 45. In addition, wings 78 and 80 perform a useful function during use of the sensor assembly 15. Thus, wings 78 and 80 act as heat insulators to reduce the temperature variation of blood in the fluid passage 41. Maintaining relatively constant temperature in the fluid passage 41 allows one to more accurately measure the compositional parameter or parameters of interest. This "heat insulator" feature is particularly applicable where the housing top 45 is made of a heat insulating material, e.g., a polymeric material. If desired, transmission block 65 may provide heat to aid in maintaining the temperature in fluid passage 41.

In one useful embodiment, housing top 45 is made of a material which is substantially gas impermeable. This feature reduces the escape of blood gases, e.g., oxygen and carbon dioxide, through housing top 45 and increases the accuracy of blood gas measurements. Housing base 35 may be made of the same or different material relative to housing top 45. However, it is important that at least a portion of housing base 35 be transparent to the light signals being sent and received by transmission block 65.

In use, housing base 35 is fitted onto the distal end 85 of transmission block 65. Distal end 85 is uniquely shaped and recess 38 is correspondingly shaped so that distal end 85 is received by and fitted into recess 38 in a manner to insure proper alignment between optical fibers 77, 79 and 81 and sensors 67, 69 and 71, respectively. Such alignment is illustrated in FIGS. 5 and 6. Housing base 35 is held in place on the distal end 85 of transmission block 65 by a movable securement assembly, shown generally at 87. Assembly 87 includes two (2) swingable arms 89 attached to either side of transmission block 65. A securement member 91, which extends outwardly from arms 89, includes a threaded hole 93 which is located directly above housing top 45 when arms 89 are in the upright position, as shown in FIG. 3.

A threaded screw 95 is provided and includes threads which matingly engage the threads of threaded hole 93. With housing base 35 in place on distal end 85 of transmission block 65 and arms 89 in the upright position, threaded screw 95 can be threaded through threaded hole 93 and made to impact housing top 45. With screw 95 contacting housing top 45, housing base 35 is secured in place in proper relation to transmission block 65. When it is desired to remove housing base 35 from transmission block 65, screw 95 is simply threaded back up hole 93, and arms 89 are swung down from the upright position. The housing base 35 is then free to be removed from the transmission block 65.

Transmission block 65 is of such a size that it can be easily and conveniently "worn" on the arm of the patient whose blood is being analyzed, as shown in FIG. 1. This feature reduces the amount of blood which is withdrawn from the patient, and also reduces the distance the blood must traverse along tube 33 in order to get the desired analyses. The transmission block 65 may be secured to the patient by means of strip 97, which is made up of hook and loop fasteners, e.g., Velcro fasteners. Of course, other means, e.g., conventional means, may be employed to removably secure transmission block 65 to the patient.

Assembly 11 functions as follows. During "normal" operation, stopcock 25 is in position (1) and a supply of flush solution from source 19 is passed through first conduit 21, flow passage 41 and second conduit 33 into the patient. Using this configuration the blood pressure of the patient can be monitored. When it is desired to chemically analyze the patient's blood, stopcock 25 is placed in position (2).

Piston 31 is then lifted away from stopcock 25. This creates a vacuum in first conduit 21 and second conduit 33 which, in turn, causes blood, from the patient, to flow through second conduit 33 into fluid passage 41 and part way into first conduit 21. At this point, optical fibers 77, 79 and 81 are activated so that signals in response to the carbon dioxide concentration, the pH and the oxygen concentration of the blood in fluid passage 41 can be obtained form sensors 67, 69 and 71, respectively.

After these signals have been transmitted for a satisfactory period of time to instrument 83, piston 31 is moved toward stopcock 25, thereby creating a positive pressure in first conduit 21 to urge the blood in first conduit 21, fluid passage 41 and second conduit 33 back into the patient. After, the blood has been returned, stopcock 25 is returned to position (1) and flush fluid from source 19 is allowed to flow through first conduit 21, flow passage 41 and second conduit 33 into the patient. Substantially all of the blood in fluid passage 41 is returned to the patient so that no blood coagulation or other buildup is apparent. This feature is important since it allows the patient's blood to be repeatedly analyzed with reliable and reproducible accuracy without creating conditions, e.g., blood clotting, which might harm the patient.

Housing base 35 is made of a transparent material, in particular a transparent polymeric material. Such transparency allows the signals from the sensors 67, 69 and 71 to be readily communicated to optical fibers 77, 79 and 81, respectively. In addition, housing base 35 and housing top 45 are each made of materials which are substantially impermeable to the liquid blood in fluid passage 41. This feature effectively isolates transmission block 65 from exposure to the patient's blood.

After use, the securement assembly 87 is released, thereby allowing the housing base 35 to be removed from the distal end 85 of transmission block 65. The components of assembly 11 which have been exposed to the patient's blood, e.g., second conduit 33, housing base 35, housing top 45 and first conduit 21, are preferably disposed of. Transmission block 65 and instrument 83, which have not been exposed to the patient's blood, can be reused repeatedly. This feature represents a substantial advantage for the present system. Thus, the relatively inexpensive components of the sensor assembly 15 can be economically discarded after a single use, e.g., use by a single patient. The much more expensive components of the sensor assembly 15 are kept isolated from the patient's blood so that they are not exposed to such blood and are available for repeated reuse without danger of cross-patient blood contamination.

Although exemplary embodiments of the invention have been shown or described, many changes, modifications and substitutions may be made by one having ordinary skill in the art without necessarily departing from the spirit and scope of this invention.

What is claimed is:

1. A sensor cassette for use in measuring a compositional parameter of the blood of a patient comprising:
    a housing adapted and sized to be located outside the body of the patient and having a fluid flow passage therethrough which is capable of receiving blood from the patient; and
    a sensing element located in said housing in or near said fluid flow passage for providing a signal in response to a compositional parameter of blood, said fluid flow passage at or near the location of said sensing element being at least 4.8 times as wide as its depth, the depth of said fluid flow passage extending directly outwardly from said sensing element and the wide direction of said fluid flow passage being substantially perpendicular to both the general direction of fluid flow in said fluid flow passage and to the depth of the fluid flow passage.

2. The senor cassette of claim 1 wherein said sensing element is an optical sensing element.

3. The senor cassette of claim 1 wherein said sensing element is a fluorescent sensing element.

4. The sensor cassette of claim 1 which comprises a plurality of sensing elements in said housing, each of said sensing elements providing a signal in response to a different compositional parameter of blood.

5. The senor cassette of claim 1 wherein said housing includes an indent opening in said fluid flow passage, said indent containing at least a portion of said sensing element.

6. A sensor cassette for use in measuring a compositional parameter of the blood of a patient comprising:
    the housing adapted and sized to be located outside the body of the patient and having a fluid flow passage therethrough into which blood can be received from said patient, said housing including a first housing component having a first recess and a second housing component having a second recess which confronts the first recess, said second housing component being at least partially received in said first recess so that at least a portion of each of said first and second recesses forms at least a portion of said fluid flow passage and a substantially annular space exists between said first and second housing components;

adhesive means located at least partially in said substantially annular space and acting to bond said first and second housing components together; and a sensing element located in said housing in or near said fluid flow passage for providing a signal in response to a compositional parameter of blood.

7. The senor cassette of claim 6 wherein said sensing element is an optical sensing element.

8. A sensor cassette as defined in claim 6 wherein said first housing component has two holes and said second housing component has two tabs, said tabs being received into said holes, respectively, to form parts of said fluid flow passage adjacent opposite ends of said fluid flow passage.

9. A sensor cassette as defined in claim 6 wherein the housing includes first and second tubing fittings located adjacent opposing ends of said fluid flow passage and adapted to hold first and second segments of hollow tubing so that said first and second segments of hollow tubing are oriented in substantially opposing directions substantially perpendicular to the general direction of flow in said fluid flow passage.

10. A sensor cassette for use in measuring a compositional parameter of the blood of a patient comprising:
a housing adapted and sized to be located outside the body of the patient and having a fluid flow passage therethrough into which blood from said patient can pass, said housing including a first housing component having two holes and a second housing component having two tabs, said tabs being received into said holes, respectively, to form parts of said fluid flow passage adjacent opposite ends of said fluid flow passage; and
a sensing element located in the housing in or near the fluid flow passage for providing a signal in response to a compositional parameter of the blood.

11. A sensor cassette as defined in claim 10 wherein the first housing component includes first and second tubing fittings adjacent opposite ends of the fluid flow passage.

12. A sensor cassette as defined in claim 11 wherein the tubing fittings are adapted to hold first and second segments of hollow tubing so that said first and second segments of hollow tubing are oriented in substantially opposing directions substantially perpendicular to the general direction of flow in said fluid flow passage.

13. A sensor cassette for use in measuring a compositional parameter of the blood of a patient comprising:
a housing adapted and sized to be worn on the body of the patient and having a fluid flow passage therethrough into which blood from said patient can be passed, said housing including first and second tubing fittings located adjacent opposing ends of said fluid flow passage and adapted to hold first and second segments of hollow tubing so that said first and second segments of hollow tubing are oriented in substantially opposing directions substantially perpendicular to the general direction of flow in said fluid flow passage; and
a sensing element located in said housing in or near said fluid flow passage for providing a signal in response to a compositional parameter of blood.

14. The sensor cassette of claim 13 wherein said mutually substantially opposing directions are substantially coplanar.

15. A sensor cassette for use in measuring a compositional parameter of the blood of a patient comprising:
a housing adapted and sized to be located outside the body of the patient and having a fluid flow passage therethrough into which blood from said patient can be passed, said housing including first and second housing components defining said fluid flow passage, said fluid flow passage being substantially impermeable to blood, said first housing component being substantially transparent; and
an optical sensing element carried by said substantially transparent first housing component in or near said fluid flow passage for providing an optical signal through said first housing component in response to a compositional parameter of blood.

16. A sensor cassette as defined in claim 1 wherein said housing includes a first housing component having a first recess and a second housing component having a second recess which confronts the first recess, said second housing component being at least partially received in said first recess so that at least a portion of each of said first and second recesses forms at least a portion of said fluid flow passage and a substantially annular space exists between said first and second housing components, and adhesive means located at least partially in said substantially annular space and acting to bond said first and second housing components together.

17. A sensor cassette as defined in claim 16 wherein the first housing component has two holes and the second housing component has two tabs, said tabs being received into said holes, respectively, to form parts of said fluid flow passage adjacent opposite ends of said fluid flow passage.

18. A sensor cassette as defined in claim 16 wherein said first housing component defines a portion of said fluid flow passage and includes first and second tubing fittings for securing first and second segments of hollow tubing to said housing and first portions of first and second fluid flow channels which form end portions of said fluid flow passage, said second housing component defines a portion of said fluid flow passage and includes second portions of said first and second fluid flow channels.

19. A sensor cassette as defined in claim 16 wherein the housing includes first and second tubing fittings located adjacent opposing ends of said fluid flow passage and adapted to hold first and second segments of hollow tubing so that said first and second segments of hollow tubing are oriented in substantially opposing directions substantially perpendicular to the general direction of flow in said fluid flow passage.

20. A sensor cassette as defined in claim 1 wherein said housing includes a first housing component having two holes and a second housing component having two tabs, said tabs being received into said holes, respectively, to form parts of said fluid flow passage adjacent opposite ends of said fluid flow passage.

21. A sensor cassette as defined in claim 20 wherein the first housing component includes first and second tubing fittings located adjacent opposing ends of said fluid flow passage and having tubing retention sections which are oriented in substantially opposing directions substantially perpendicular to the general direction of flow in said fluid flow passage.

22. A sensor cassette as defined in claim 1 wherein said housing includes a first housing component defining a portion of said fluid flow passage, said first housing component includes first and second tubing fittings for securing first and second segments of hollow tubing to said housing and first portions of first and second fluid flow channels which form end portions of said fluid flow passage, said second housing component defining a portion of said fluid flow passage and including second portions of said first and second fluid flow channels.

23. A sensor cassette as defined in claim 1 wherein said housing includes first and second tubing fittings located adjacent opposing ends of said fluid flow passage and adapted to hold first and second segments of hollow tubing so that said first and second segments of hollow tubing are oriented in substantially opposing directions substantially perpendicular to the general direction of flow in said fluid flow passage.

24. A sensor cassette as defined in claim 1 wherein said housing includes first and second housing components defining said fluid flow passage, said fluid flow passage being substantially impermeable to blood, said first housing component being substantially transparent and said sensing element being carried by said substantially transparent first housing component.

25. An assembly for use in measuring a compositional parameter of blood comprising:
   a housing having a fluid flow passage extending therethrough and first and second opposite sides;
   a tube;
   means on said housing for coupling the housing to the tube with the tube in communication with said fluid flow passage whereby blood can be conducted to the fluid flow passage;
   said housing having wall means defining an external recess on said first side of the housing;
   a sensing element carried by said wall means for providing a signal in response to a compositional parameter of the blood;
   signal transmission means for transmitting said signal away from the housing, a portion of said signal transmission means being receivable in said recess; and
   coupling means carried by the signal transmission means for engaging said second side of said housing to releasably couple the housing to the signal transmission means.

26. An assembly as defined in claim 25 wherein said coupling means includes a coupling member pivotally mounted on the signal transmission means and pivotable between a locking position in which the coupling member engages said second side of said housing to releasably couple the housing to the signal transmission means and a releasing position in which the housing can be removed from the signal transmission means.

27. An assembly as defined in claim 25 wherein the sensing element is optical and the wall means is substantially transparent at the sensing element.

28. The assembly of claim 25 wherein said sensing element is an optical sensing element.

29. The assembly of claim 25 wherein said sensing element is a fluorescent sensing element.

30. The assembly of claim 25 including a plurality of sensing elements, each of said sensing elements providing a signal to a signal transmission means in response to a different compositional parameter of blood located in said fluid flow passage.

31. The assembly of claim 25 which further comprises volume oscillator means in fluid communication with said fluid flow passage for urging blood to flow in said fluid flow passage.

32. The assembly of claim 25 wherein said housing includes an indent open to said fluid flow passage, said indent containing at least a portion of said sensing element.

33. The assembly of claim 25 wherein the cross-sectional area of said fluid flow passage at or near the location of said sensing element is less than about 10 times the largest cross-sectional area of said tube available for fluid flow.

34. The assembly of claim 25 wherein the cross-sectional area of said fluid flow passage at or near the location of said sensing element is less than about 3 times the largest cross-sectional area of said tube available for fluid flow.

35. A sensor cassette for use in measuring a compositional parameter of the blood of a patient comprising:
   a housing adapted and sized to be located outside the body of the patient and having a fluid flow passage extending therethrough, said fluid flow passage being elongated along an axis of elongation and having first and second ports at opposite ends of the fluid flow passage and located along the axis of elongation, said fluid flow passage being capable of receiving blood from the patient through one of said ports;
   a plurality of sensing elements located in said housing along the axis of elongation in or near said fluid flow passage, each of said sensing elements being capable of providing a signal in response to a different compositional parameter of blood; and
   said fluid flow passage at or near the location of said sensing element being at least two times as wide as its depth, the depth of said fluid flow passage extending directly outwardly from said sensing element and the wide direction of said fluid flow passage being substantially perpendicular to both the general direction of fluid flow in said fluid flow passage and to the depth of the fluid flow passage.

36. An assembly including the sensor cassette of claim 35 and first and second conduits coupled to the sensor cassette in communication with the first and second ports, respectively, the cross-sectional area of the fluid flow passage being about 2.2 times the largest cross-sectional area of either of said conduits available for fluid flow.

* * * * *

UNITED STATES PATENT AND TRADEMARK OFFICE
CERTIFICATE OF CORRECTION

PATENT NO. : 4,989,606
DATED : February 5, 1991
INVENTOR(S) : John L. Gehrich et al.

It is certified that error appears in the above-identified patent and that said Letters Patent is hereby corrected as shown below:

Col. 7, line 17, "from" should be --form--.
Col. 10, line 42, "senor" should be --sensor--.
Col. 10, line 44, "senor" should be --sensor--.
Col. 10, line 50, "senor" should be --sensor--.

Col. 11, line 7, "senor" should be --sensor--.

Signed and Sealed this

Eighteenth Day of May, 1993

Attest:

MICHAEL K. KIRK

*Attesting Officer*   Acting Commissioner of Patents and Trademarks